United States Patent
Simpson et al.

(10) Patent No.: US 10,393,644 B2
(45) Date of Patent: Aug. 27, 2019

(54) METHOD AND SYSTEM FOR MICROFLUIDIC PARTICLE ORIENTATION AND/OR SORTING

(71) Applicant: Engender Technologies Limited, Auckland (NZ)

(72) Inventors: Miriam Cather Simpson, Auckland (NZ); Charles Alan Rohde, Santa Fe, NM (US)

(73) Assignee: Engender Technologies Limited, Auckland (NZ)

( * ) Notice: Subject to any disclaimer, the term of this patent is extended or adjusted under 35 U.S.C. 154(b) by 0 days.

(21) Appl. No.: 15/697,770

(22) Filed: Sep. 7, 2017

(65) Prior Publication Data
US 2017/0370822 A1    Dec. 28, 2017

Related U.S. Application Data

(62) Division of application No. 14/417,622, filed as application No. PCT/NZ2013/000135 on Jul. 29, 2013, now Pat. No. 9,784,663.
(Continued)

(51) Int. Cl.
*B01L 3/00* (2006.01)
*G01N 15/00* (2006.01)
(Continued)

(52) U.S. Cl.
CPC ...... *G01N 15/1456* (2013.01); *B01L 3/50273* (2013.01); *B01L 3/502761* (2013.01);
(Continued)

(58) Field of Classification Search
CPC ............. B01L 3/5027; B01L 3/502761; G01N 15/1425; G01N 15/1427; G01N 15/1459; G01N 15/1484
(Continued)

(56) References Cited

U.S. PATENT DOCUMENTS 6,778,724 B2    8/2004  Wang et al.
7,068,874 B2 *  6/2006  Wang ...................... H05H 3/04
                                                    250/432 R
(Continued)

FOREIGN PATENT DOCUMENTS

EP          1563908 B1      12/2010
JP       H 07104191 A        4/1995
WO    WO 02/087792 A1       11/2002

OTHER PUBLICATIONS

Dean, P.N. et al., "Hydrodynamic Orientation of Sperm Heads for Flow Cytometry," Biophysics Journal, vol. 23, 1978, pp. 7-13.
(Continued)

*Primary Examiner* — Terrell H Matthews
(74) *Attorney, Agent, or Firm* — Cooley LLP; Ivor R. Elrifi; Brian P. Hopkins

(57) ABSTRACT

A system for orienting particles in a microfluidic system includes one or more radiation pressure sources arranged to expose particles to radiation pressure to cause the particles to adopt a particular orientation in the fluid. A system for sorting particles in a microfluidic system includes a detection stage arranged to detect at least one difference or discriminate between particles in the fluid flow past the detection stage, and one or more radiation pressure sources past which the particles move sequentially and a controller arranged to switch radiation energy to cause a change in direction of movement of selected particles in the fluid flow to sort the particles. The particles may be biological particles such as spermatozoa. The radiation pressure may be optical pressure and may be from one or more waveguides which may extend across a channel of the microfluidic system.

13 Claims, 10 Drawing Sheets

Related U.S. Application Data

(60) Provisional application No. 61/676,391, filed on Jul. 27, 2012.

(51) Int. Cl.
*G01N 15/14* (2006.01)
*G01N 21/64* (2006.01)
*G01N 15/10* (2006.01)
*G01N 15/02* (2006.01)

(52) U.S. Cl.
CPC ..... *G01N 15/1425* (2013.01); *G01N 15/1427* (2013.01); *G01N 15/1459* (2013.01); *G01N 15/1484* (2013.01); *G01N 21/6428* (2013.01); *B01L 2200/0652* (2013.01); *B01L 2300/0663* (2013.01); *B01L 2300/0816* (2013.01); *B01L 2300/0874* (2013.01); *B01L 2300/0887* (2013.01); *B01L 2300/14* (2013.01); *B01L 2400/0454* (2013.01); *B01L 2400/0487* (2013.01); *G01N 2015/0065* (2013.01); *G01N 2015/0288* (2013.01); *G01N 2015/1006* (2013.01); *G01N 2015/149* (2013.01)

(58) Field of Classification Search
USPC .......................................................... 209/552
See application file for complete search history.

(56) References Cited

U.S. PATENT DOCUMENTS

| | | | | |
|---|---|---|---|---|
| 7,472,794 B2* | 1/2009 | Oakey | .................... | B01D 57/02 209/210 |
| 7,676,122 B2* | 3/2010 | Dou | ........................ | B07C 5/342 210/600 |
| 7,758,811 B2* | 7/2010 | Durack | ................. | C12N 5/0612 422/73 |
| 8,120,770 B2* | 2/2012 | Huang | ................ | B01F 13/0062 209/208 |
| 8,134,705 B2* | 3/2012 | Kaduchak | .......... | G01N 15/1404 356/337 |
| 8,162,149 B1* | 4/2012 | Perroud | ............. | G01N 15/1484 209/155 |
| 8,529,760 B1* | 9/2013 | Hart | ........................ | B01J 19/121 204/600 |
| 9,239,302 B2* | 1/2016 | Pidcock | ............. | G01N 23/087 |
| 9,488,621 B2 | 11/2016 | Kaduchak et al. | | |
| 9,784,663 B2* | 10/2017 | Simpson | ............. | G01N 15/1459 |
| 2002/0181837 A1* | 12/2002 | Wang | ...................... | H05H 3/04 385/16 |
| 2005/0164158 A1 | 7/2005 | Wang et al. | | |
| 2006/0163119 A1 | 7/2006 | Hirano et al. | | |
| 2008/0138010 A1 | 6/2008 | Dou et al. | | |
| 2008/0261295 A1* | 10/2008 | Butler | ............... | B01L 3/502761 435/286.5 |
| 2009/0014360 A1* | 1/2009 | Toner | ................. | B01D 21/0087 209/208 |
| 2009/0158823 A1* | 6/2009 | Kaduchak | .......... | G01N 15/1404 73/61.75 |
| 2011/0008767 A1* | 1/2011 | Durack | ................. | B01L 3/5027 435/5 |
| 2014/0273192 A1* | 9/2014 | Sharpe | ............. | B01L 3/502761 435/288.7 |
| 2016/0003729 A1* | 1/2016 | Lo | ...................... | G01N 15/1459 435/288.7 |

OTHER PUBLICATIONS

Wang, M. et al., "Microfluidic sorting of mammalian cells by optical force switching," *Nature Biotechnology* (2005) 23 (1): 83-87.

\* cited by examiner

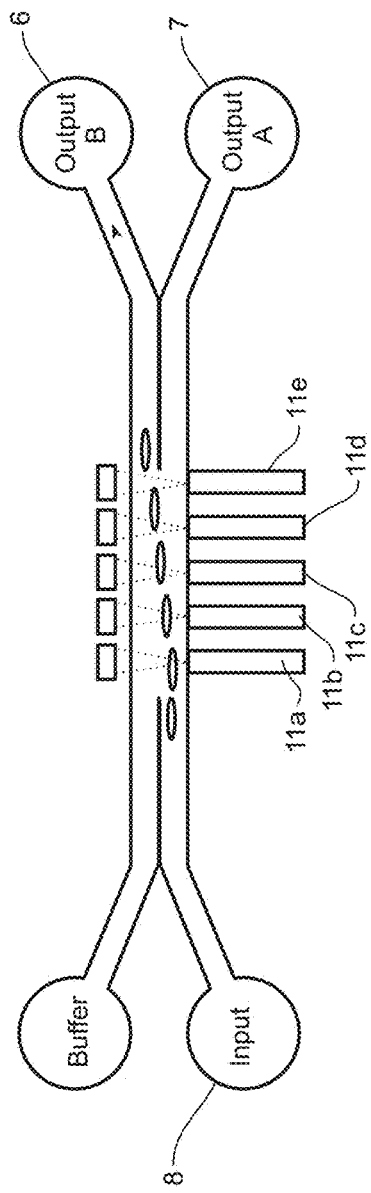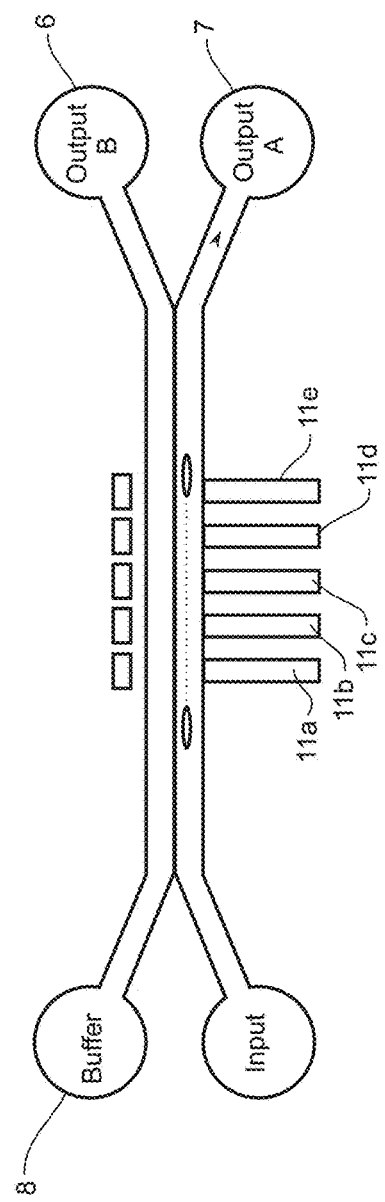

METHOD AND SYSTEM FOR MICROFLUIDIC PARTICLE ORIENTATION AND/OR SORTING

CROSS-REFERENCE TO RELATED APPLICATIONS

This application is a divisional application of U.S. Ser. No. 14/417,622, filed Jan. 27, 2015, which is a national stage application, filed under 35 U.S.C. 371, of International Application No. PCT/NZ2013/000135, filed Jul. 29, 2013, which claims the benefit of, and priority to, U.S. Ser. No. 61/676,391, filed Jul. 27, 2012. The contents of each of these applications is incorporated by reference in their entirety.

FIELD OF INVENTION

The invention relates to a method and system for particle orientation and/or sorting in a microfluidic system.

BACKGROUND

Developments in commercial and academic medical and biotechnology have driven a strong focus on methods for biological cell sorting. The two main approaches that have emerged—bulk separation and single cell sorting—both enrich a population of cells with a targeted subset with specific physicochemical (i.e. size, volume, light scattering properties, etc.), immunological, or functional characteristics. Bulk sorting generally focuses upon a single discriminating cellular feature. Examples include cell filtration, centrifugation/sedimentation and affinity-based panning methods. The main disadvantages of bulk sorting are lower purity, loss of cells during the sorting process, difficulty in sorting out relatively rare cells, and difficulty in discriminating among similar sub-populations of cells. Bulk sorting, however, is a relatively simple method that offers high throughput. In contrast, single cell methods, the most important of which is fluorescence activated cell sorting (FACS) by flow cytometry, examine each cell individually to target the desired subpopulation for isolation and then guide them into different output streams. The reduction in throughput is offset by major advantages in specificity of sorting that is tunable to the desired outcome, generally higher recovery of cells, the ability to sort rare or only weakly discriminated cell populations, and the availability of multi-target sorting based on an array of multiple cellular features (i.e. several types of surface receptor, each tagged with a different fluorescent label). One important challenge faced by FACS flow cytometric methods is the damage incurred by some cells in the flow (shear stress) and sorting (electric field damage) processes. An important example is the reduced fertility of sorted sperm samples that can be attributed to these disruptive physical processes.

In the agriculture sector, cell discrimination is particularly important in livestock species where artificial insemination is commonly practised such as cattle. The use of sexed semen facilitates control of offspring gender for commercial benefit. The current commercially important method for sperm sorting uses FACS flow cytometry, in which sperm are discriminated by their differences in DNA content. The DNA of each spermatazoon is stained with a fluorescent dye in proportion to the DNA content. As the X chromosome is larger (i.e. has more DNA) than the Y chromosome, the "female" (X-chromosome bearing) spermatozoa will absorb a greater amount of dye than the "male" (Y-chromosome bearing) spermatozoa and as a consequence when exposed to UV light during flow cytometry will fluoresce with higher intensity than the Y spermatozoa. Before detection or discrimination the sperm may be oriented hydrodynamically and the sperm may be separated into individual droplets that then may be electrically charged. After detection or discrimination, the sperm are sorted by electric field—charged droplet interactions.

SUMMARY OF THE INVENTION

In broad terms in one aspect the invention comprises a method of orienting particles in a microfluidic system, which includes exposing the particles to radiation pressure in a microfluidic system to cause at least a majority of the particles to adopt a particular orientation in the fluid.

In broad terms in another aspect the invention comprises a system for orienting particles in a microfluidic system, which includes one or more radiation pressure sources arranged to expose particles in the microfluidic system to radiation pressure to cause at least a majority of the particles to adopt a particular orientation in the fluid.

The particles may be biological or non-biological particles. Typically the particles are asymmetric particles. The asymmetry may be in any physical property that leads to an asymmetric interaction with the incident radiation, including but not limited to asymmetry in physical dimensions of the particles. In some embodiments the particles may be sperm, red blood cells, or bacteria, for example.

The radiation pressure may be optical pressure and may be from one or more waveguides which may extend across a channel of the microfluidic system, for example across above, below or across the side walls of the channel, or may abut a channel from above, below or the side. The waveguide(s) may be one or more optical waveguides are connected to a light source, such as a laser, to transport light and generate the radiation pressure also referred to as optical force, photon pressure or electromagnetic pressure. The one or more waveguides may be manufactured as part of the intrinsic process of fabricating the microfluidic system, or may be inserted as fibre optic units in the construction of the final system.

A microfluidic system for orienting particles as above may also comprise a pre-stage for focusing and/or singulating the particles into a particular location within the channel. This system may be hydrodynamic or radiation pressure based.

In broad terms in another aspect the invention comprises a method of sorting particles in a microfluidic system, which includes:
  detecting at least one difference or discriminating between particles, and
  switching based on an input from the detection or discrimination, one or more radiation pressure sources past which the particles move sequentially to cause a change in direction of movement of selected particles in the fluid flow to sort the particles.

The particles may be directed into two or more than two different outputs.

The one or more radiation pressure sources may be one or more waveguides, which may extend across a channel of the microfluidic system, for example across above, below or across the sidewalls of the channel, or may abut a channel from above, below or the side.

The step of detecting at least one difference or discriminating between particles may comprise an optical technique for assessing a characteristic of the particle, the technique may be a fluorescence-based detection technique.

The method may also comprise singulating particle flow and may also comprise focusing the particles to a particular location within the channels. The forces may be hydrodynamic or radiation pressure based.

The method may also comprise causing at least a majority of the particles to first adopt a particular orientation in the fluid before detecting, where the particles are asymmetric particles. The orientation step may comprise exposing the particles to radiation pressure such as optical pressure to cause at least a majority of the particles to adopt a particular orientation in the fluid.

In broad terms in another aspect the invention comprises a system for sorting particles in a microfluidic system, which includes:

a detection stage arranged to detect at least one difference or discriminate between particles in the fluid flow past the detection stage, and one or more radiation pressure sources past which the particles move sequentially and a controller arranged to switch based on an input from the detection or discrimination stage, radiation energy in the one or more radiation pressure sources to cause a change in direction of movement of selected particles in the fluid flow to sort the particles.

The system may be arranged to switch or sort the particles so that each particle is directed into one of two or one of more than two different outputs.

The one or more radiation pressure sources may be one or more waveguides which may extend at least partway across a channel of the microfluidic system, for example across above, below or across the side walls of the channel, or may abut the channel from above, below or the side.

The detection stage may be arranged to detect or discriminate particles by an optical technique such as a fluorescence-based detection technique.

The particles may be biological or non-biological particles. Typically the particles are asymmetric particles. The asymmetry may be in any physical property that leads to an asymmetric interaction with the optical force, including but not limited to asymmetry in physical dimensions. In some embodiments the particles may be sperm, red blood cells, bacteria, or nanoparticles for example.

A microfluidic system for orienting particles as above may also comprise a pre-stage singulating particle flow and may also comprise a pre-stage for focusing the particles into a particular location within the channel. This system may be hydrodynamic or optical.

The system may also comprise an orientation stage arranged to cause at least a majority of the particles to first adopt a particular orientation in the fluid, particularly where the particles are asymmetric particles. The orientation stage may comprise one or more waveguides arranged to in use expose particles to radiation such as optical pressure to cause at least a majority of the particles to adopt a particular orientation in the fluid.

In broad terms in another aspect the invention comprises a microfluidic system for sexing sperm which includes:

one or more orienting radiation pressure sources arranged to expose sperm to pressure to cause individual sperm to adopt a common orientation in the fluid a fluorescence-based detection stage arranged to discriminate male and female sperm in the fluid flow past the detection stage, and one or more switching radiation pressure sources s past which the individual sperm subsequently move, and a controller arranged receive an input from the detection stage and to control radiation energy in the one or more switching radiation pressure sources to separately direct male and/or female sperm.

A microfluidic system for orienting particles as above may also comprise a pre-stage for singulating sperm flow and a pre-stage for focusing the sperm into a particular location within the channel. This system may be hydrodynamic or optical.

The term "comprising" as used in this specification means "consisting at least in part of". When interpreting statements in this specification which include that term, the features prefaced by that term in each statement all need to be present but other features can also be present. Related terms such as "comprise" and "comprised" are to be interpreted in the same manner.

BRIEF DESCRIPTION OF THE DRAWINGS

The invention is further described with reference to the accompanying figures in which.

DETAILED DESCRIPTION OF THE PREFERRED EMBODIMENTS

Figure 1:
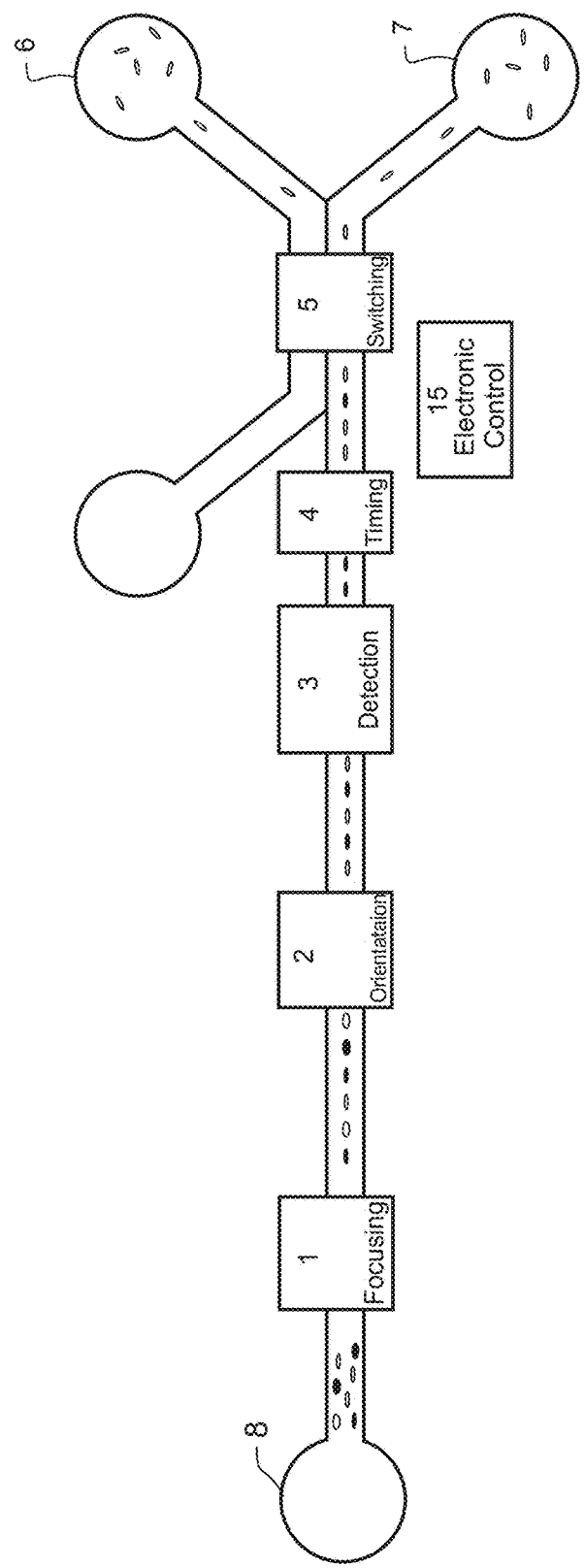
FIG. 1 schematically illustrates an embodiment of a microfluidic system of the invention for particle sorting, FIGS. 2a and 2b schematically illustrate embodiments for particle orientation in which a single waveguide—FIG. 2a, or multiple waveguides—FIG. 2b, abut the microchannel from above, below or from a side of the channel, FIGS. 3a and 3b schematically illustrate embodiments for particle orientation in which a single waveguide—FIG. 3a, and multiple waveguides—FIG. 3b, extend across the microchannel above, below or along a side wall of the channel, FIGS. 4a and 4b schematically illustrate embodiments for sorting or switching selected particles in a fluid flow in a microchannel, in which multiple waveguides abut the channel from above, below or from a side of the channel, FIGS. 5a and 5b schematically illustrate embodiments for sorting or switching selected particles in a fluid flow in a microchannel, in which multiple waveguides extend across the channel above, below or along the side wall of the channel.

Referring to FIG. 1 the microfluidic system typically provided on a microfluidic chip for particle orientation and sorting comprises focusing, orientation, detection of a discriminating feature that may be fluorescence, and timing and switching stages sequentially along a microchannel along which the particles move with the fluid flow in the channel, from one stage to the next.

In the embodiment shown a hydrodynamic focusing and/or singulating stage 1 places the particles in a particular location in the channel.

If the particles are asymmetric, such as sperm for example, the initial orientation of the particles may be random, and an orientation stage 2 orients the particles substantially all or at least a majority with a common orientation predetermined relative to the channel geometry. In the schematic figure the particles are shown being oriented vertically. In a preferred embodiment the particles are oriented at the orientation stage by optical forces such as from an optical waveguide as will be further described. One or more waveguides may extend across the channel, for example across above, below or along the side wall of the channel, or may abut the channel from above, below or from the side of the channel. The waveguide may form part of the channel wall, or may be physically separated from the microfluidic chamber.

In this embodiment the detection stage 3 is a fluorescence-based detection stage and the particles are previously stained with a fluorescent dye, and the fluorescence detection stage 3 evaluates the fluorescence intensity of each particle and passes fluorescence information to timing and switching stages 4 and 5, which switch or sort the particles so that each particle is directed into one of two different outputs 6 and 7. The timing and switching stages 4 and 5 are controlled by an electronic controller 15. For example the particles may be sperm and male sperm may be directed to output 6 and female sperm to output 7 for example. Alternatively particles may be sorted to select one particle type which is desired from another particle type which is non-desired for the particular application, such as to select red blood cells for example and in such an embodiment the desired particles may be directed to collection or to further processing while the undesired particles may be directed to waste or an outlet to waste or some other processing.

The particles enter the microfluidic system from source 8. In the figure the source 8 and outputs 6 and 7 are schematically shown as collection volumes such as chambers for containing the particles, but the particles may enter the system or the sorting section of the microfluidic system, from a microfluidic channel or channels from a prior processing stage and exit the sorting section to microfluidic channels carrying the particles to other subsequent processing for example.

Figure 2A:
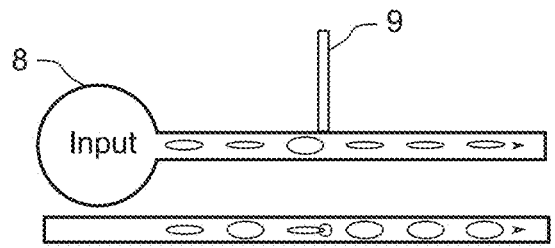
Figure 2B:
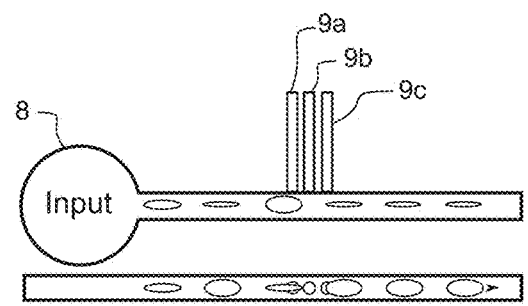

FIGS. 2*a* and 2*b* schematically illustrate embodiments for particle orientation in which a single waveguide—FIG. 2*a*, or multiple waveguides—FIG. 2*a*, abut the microchannel from a side (above, below or from either side) of the channel, which may be used in the orientation stage 2 of the system of FIG. 1. In FIG. 2*a*, a radiation waveguide 9 such as an optical fibre connected to a source such as a laser abuts the channel from one side of the channel. The waveguide may form part of the wall of the channel or may be physically separated from the microfluidic chamber. As asymmetric particles in random orientation pass the terminus of the waveguide 9, they are subjected to an optical force which tends to cause the asymmetric particles to orient with a common and predetermined orientation. In the embodiment of FIG. 2*b*, the particles pass three waveguides 9*a*-9*c* in a series, which cumulatively orient the particles. The optical force from the first waveguide 9*a* may cause each particle to begin rotating towards a desired orientation, while optical force from subsequent waveguides 9*b* and 9*c* continues to cause the particle to move to the desired orientation. FIG. 2*a* shows a single waveguide abutting the side of the channel and FIG. 2*b* three waveguides abutting the side of the channel but alternative embodiments may comprise two or more than three waveguides, and the waveguides may abut the channel from above, below or from either side.

Waveguides may be manufactured as part of the device (i.e. in situ) or inserted during device assembly (i.e. fibre optic components). Typically the waveguides may apply optical force in an optical wavelength range from the visible to near-infrared (500 nm-2 µm), and laser light sources will be CW emission sources with output powers of less than 1 W/waveguide, to minimise the optical forces applied in each interaction with the particle. The emission of the laser light may be controlled electronically, to switch on and off as desired to generate pulses on the microsecond to millisecond timescale.

Figure 3A:
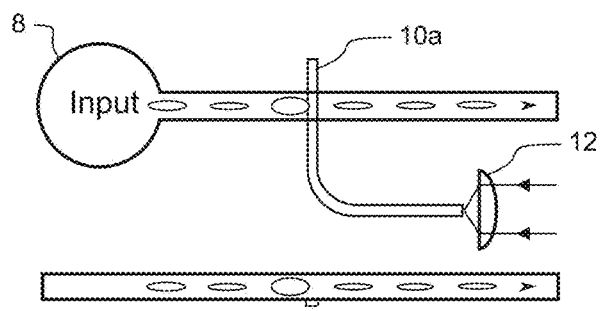
Figure 3B:
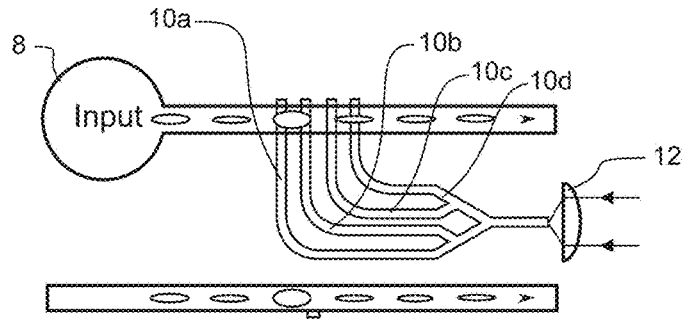

FIGS. 3*a* and 3*b* schematically illustrate embodiments for particle orientation in which a single waveguide 10*a*—FIG. 3*a*, and multiple waveguides 10*a*-10*d*—FIG. 3*b*, extend across the microchannel above or below the channel. The waveguide(s) extend above, below or along a side wall of the microchannel so that the particles pass by the waveguides, and in doing so are subject to radiation emanating from the waveguides and which applies photon pressure to orient the particles described above. Optical radiation may be supplied to the waveguide(s) from a coupling lens 12 as shown.

An advantage of the waveguide-based orientation embodiments described above, over particle orientation via hydrodynamic pressure as commonly used in sperm sexing with conventional flow cytometry for example, is that less force is applied to the particles such as sperm to orient them, so that there is a lower likelihood of particle damage during or as a result of the particle orientation. This may be particularly so for the embodiments of FIGS. 2*b* and 3*b* which orient the particles via a series of sequential waveguides each applying lower radiation pressure than would be required to orient the same particles with radiation pressure from a single waveguide. This may be particularly advantageous for biological particles such as sperm, and cells for example.

Figure 5A:
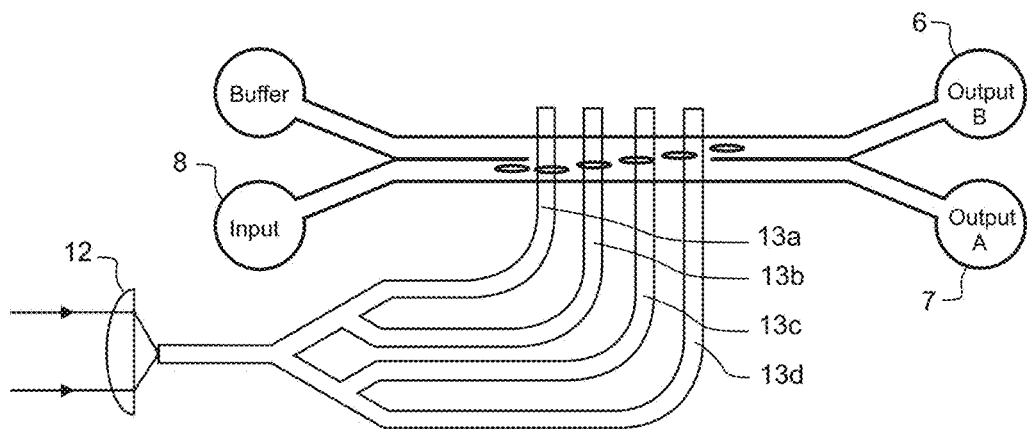
Figure 5B:
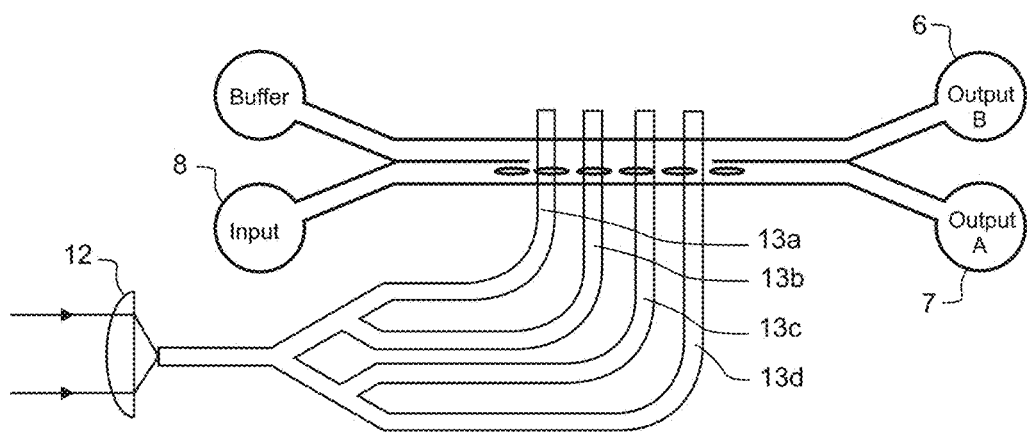

FIGS. 4*a* and 4*b* show an embodiment for sorting or switching selected particles to change the direction of movement in the fluid flow in the microchannel, in which the multiple waveguides 11a-11e abut the channel from a side of (or above or below) the channel. FIGS. 5a and 5b show an embodiment for sorting or switching selected particles to change the direction of movement in the fluid flow in the microchannel, in which the multiple waveguides extend across the channel above, below or along side of the channel. After the fluorescence detection stage 3 (FIG. 1), in the switching stage 4 (FIG. 1) each particle passes a series of waveguides 11a-11e which enter the microchannel from the side in FIGS. 4a and 4b, or 13a-13d which pass below or above the microchannel in the embodiment of FIGS. 5a and 5b. The waveguides in FIGS. 4a, 4b, 5a and 5b may form part of the wall of the channel or may be physically separated from the microfluidic chamber.

Referring to FIGS. 4a and 5a, when a particle desired to be switched to a particular output 6 or 7 passes through the switching stage 5 (see FIG. 1), the energy source to each of the waveguides 11a-11e or 13a-13d is switched on. As the particle passes the first waveguide, it is deflected by the optical force, and is further deflected as it passes the subsequent waveguides. All of the waveguides may be energised together, from a common laser source through a coupling lens 12 as shown in FIGS. 5a and 5b for example, or in a higher speed system particle movement may be timed with switching of each of waveguides 11a-11e or 13a-13d so that each waveguide is energised, one after the other, as the selected particle passes each individual waveguide. Controller 6 (see FIG. 1) with input(s) from timing stage 4 (see FIG. 1) sequences the energising of the switching waveguides with the passing the switching stage of the selected particles. In the embodiment shown, there is a laminar flow through the channel and, referring to FIGS. 4a and 5a, the waveguides when energised act to deflect selected particles from the flow on one side towards output 7 across the flow boundary and into the flow towards output 6. When the waveguides are not excited, there is no deflection of the particles which therefore continue move towards output 7, as shown in FIGS. 4b and 5b. In the embodiments shown the system is arranged to switch or sort the particles so that each particle is directed into one of two outputs 6 and 7 but in alternative embodiments the system may be arranged to switch or sort the particles between more than two different outputs such as three or four outputs for example. For example the waveguides when sequentially energised may deflect selected particles from the flow on one side across a first flow boundary and into a second flow and then across a second flow boundary and into a third flow towards a third output. Switching or sorting may be based on ternary rather than binary characteristics of the particles for example. Also in alternative embodiments the waveguides may operate to cause selected particles to deflect to turn into a different channel or channels instead of collection volumes for example.

Figure 6A:
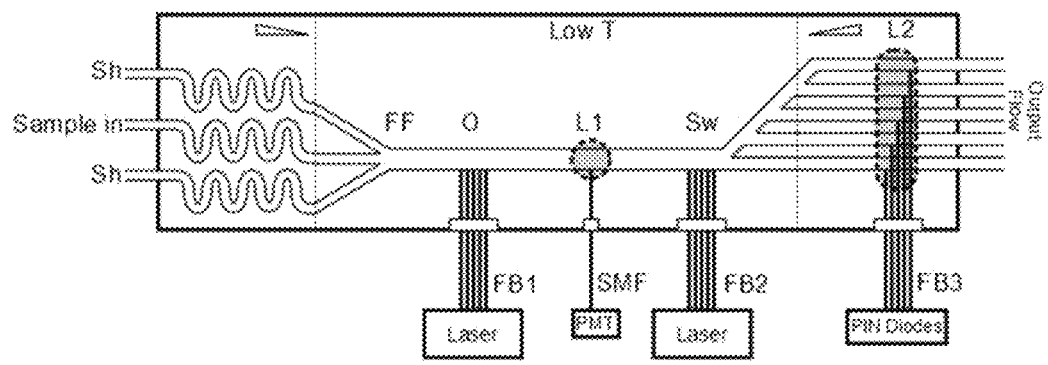
FIG. 6a shows an embodiment of a microfluidic chip the invention for performing orientation and separation of sperm and FIG. 6b shows an array of individual sorting chips may arranged for massively parallel microfluidic implementation to sort sperm according to sex.

FIG. 6a shows a microfluidic chip that incorporates an embodiment of the invention to perform orientation and separation of bovine sperm. The sperm sample, with DNA already stained and rinsed, enters the chip at Sample in, along with two sheath fluid flows Sh. The sperm sample and sheath flows are cooled by a Peltier cooling stage (not shown) beneath the chip, and maintained at low temperature throughout the on-chip processing. The sperm are focused into the desired region of the channel in region FF. They are then oriented at O using the radiation pressure from a fibre bank FB1. In this example, the fibre bank abuts the channel from the side and four single-mode fibres are shown. These fibres transmit light from a laser into the chip. After orientation, the fluorescence intensity of the sperm DNA is evaluated using a UV LED L1 illuminating the detection region from beneath the chip. The fluorescence is coupled out of the channel using single mode fibre SMF and sent to photomultiplier tube detector PMT. The output of photomultiplier tube detector PMT is used to control switching system Sw. If a sperm is selected to be directed to a new output channel, the laser sends light through second fibre bank FB2 to move the sperm in the channel to a new flow stream. The sperm then flow across a second thermal gradient to raise the temperature in a controlled fashion to a desired temperature Such as room or body temperature—note that the serpentine path required for thermal equilibrium with the gradient is not shown for the output channels for clarity. The output channels also include flow outputs for the sheath fluid and a waste stream, as well as for the X- and Y-chromosomal sperm. A white light source L2 beneath the output channels induces scattering from particles that enter the individual output channels. That scattering is detected using a third bank of fibres FB3 so that the sperm switching can be detected by Si PIN diodes and sent to the controller for counting.

Figure 6B:
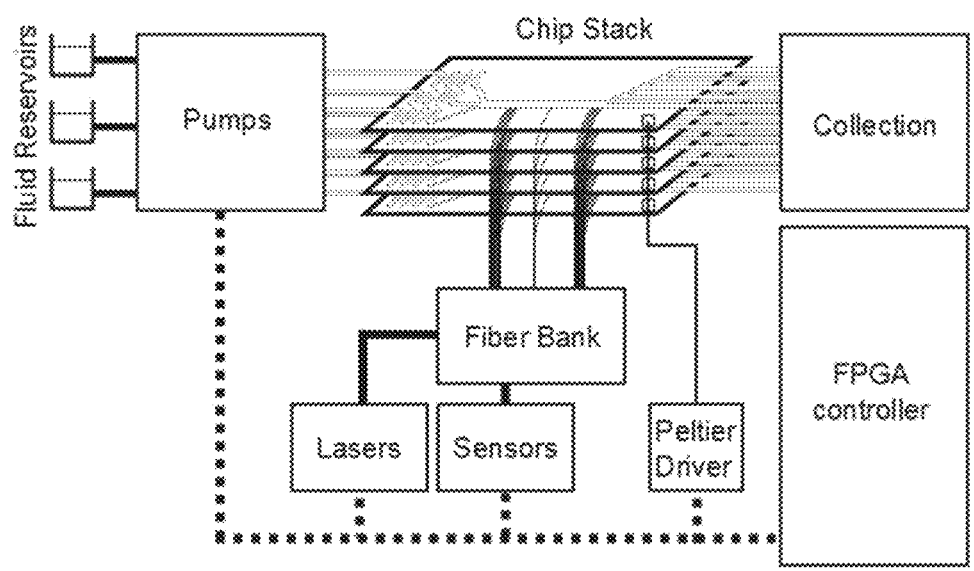

FIG. 6b shows how an array of individual sorting chips may be used to achieve bulk sorting of sperm samples. The controlling electronics, laser sources, sensors, driver for the Peltier stage (T-control) and bulk fluid input and output flow are external to the sorting chip. In this diagram, only four chips are shown, for clarity only.

Again an advantage of the waveguide-based particle switching embodiments described above, over particle switching via hydrodynamic pressure for example, is that less force is applied to the particles, and this may be particularly advantageous for biological particles such as sperm and cells for example. Thus while a waveguide-based particle switching stage as described above may be preceded by a hydrodynamic pressure-based particle orientation stage (if a particle orientation stage is required), and vice versa a waveguide-based particle orientation stage as described above may be followed by a hydrodynamic particle switching stage, in a preferred embodiment a system particularly for sorting asymmetric biological particles such as sperm may comprise a waveguide-based orientation stage arranged to orient the sperm by radiation pressure, a detection stage such as a fluorescence-based detection stage, and a waveguide-based switching stage which uses optical force to separately direct male and female sperm. The system will also have an electronic such as a microprocessor-based control system. The fluorescence detection stage 3 may be arranged to irradiate the sperm previously contacted or stained with a fluorescent marker dye which binds to the DNA of each spermatozoom, and comprises a detector to detect the intensity of the resulting fluorescence. The female absorb a greater amount of dye than the male sperm, and therefore fluoresce with higher intensity and enabling discrimination.

Systems which are comprised of only a single waveguide are restricted in their processing speed by the limited impulse (force×time) of the optical force on the particle of interest. The interaction time is limited by the physical size of the waveguide and the flow speed of the particles. The manipulation force is limited by the optical trapping potential of the waveguide. Higher forces lead to complete optical trapping, in which particles are no longer free to move with the surrounding fluid. This sets the typical use of single waveguide particle manipulation to low throughput, high precision processing of particles. Multiple waveguide orientation and switching embodiments, such as described above offer the advantage of continuous application of a well controlled optical force over an extended time without the occurrence of optical trapping. This allows for arbitrarily high throughput (particle flow speed) of particles by the serial addition of optical force producing waveguides increasing the impulse applied to the particle.

A microfluidic system of the invention for sorting sperm or the particles may have at least one microchannel with a sorting section in which the particles are processed as described above, or arrays of such sorting sections to increase throughput. Systems are preferably embodied in a small microfluidic device or chip prepared by micromachining, polymer processing techniques or other microfabrication technologies to form the microfluidic structures, and comprises supporting pumps, valving and instrumentation. Typically the microchannel(s) may have a width in the range 10 to 500 microns, or 100 to 400 microns, and a depth in the range 5 to 250 microns, for example. The dimensions of the microfluidic flow channels support laminar flow, with minimal turbulence. In the embodiments described and illustrated in the figures, the microstructure has a planar form with in-plane length and width greater than depth transverse to the plane. In alternative embodiments, the depth may be greater than the length and/or width of the microchannel and reservoir and other cavities of the microsystem. In alternative embodiments, the microchannels may extend in three directions, and may feature curved segments as well as angles. In the embodiments shown in the figures the microcavities have a rectangular or square cross-section but in alternative embodiments the microstructures may have a circular or oval cross-section for example, or a cross-section of other shape.

EXPERIMENTAL

The invention is further illustrated by way of example by the following description of simulation and trials work.

Example 1

Figure 7A:
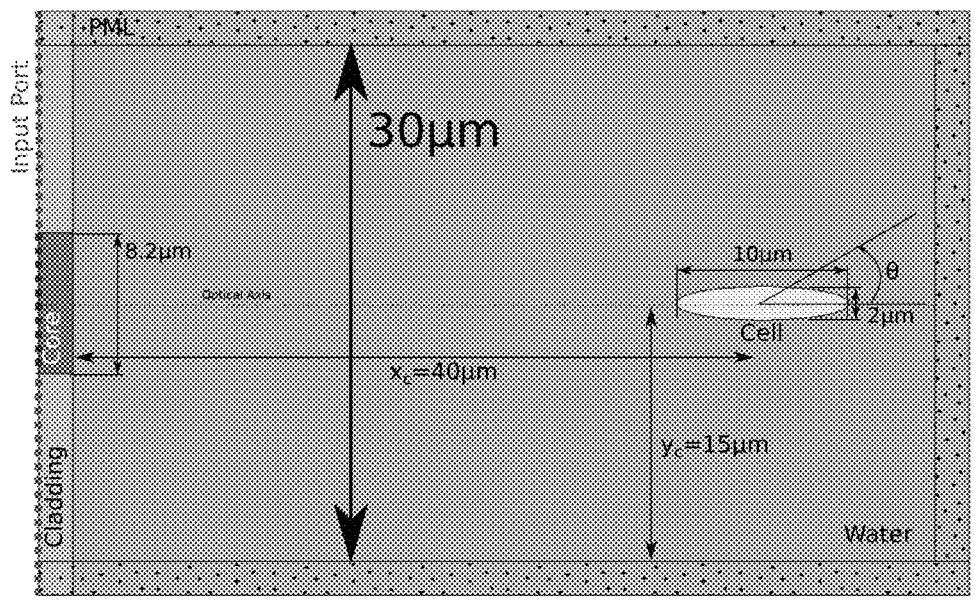
FIGS. 7a and 7b are computational geometries used in FEM simulations referred to on the subsequent description of experimental work, FIG. 7a-elliptical cylinder in water placed along the optical axis of waveguide 40 μm from terminus of waveguide and FIG. 7b-elliptical cylinder placed above an SU8 photo-epoxy waveguide with a small gap separating the cylinder from the waveguide.
Figure 7B:
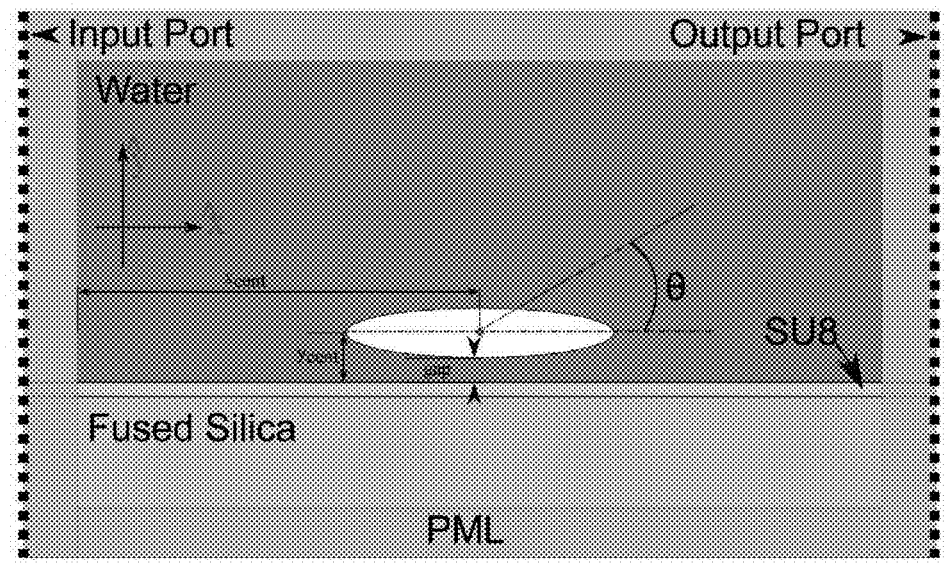
Figure 8:
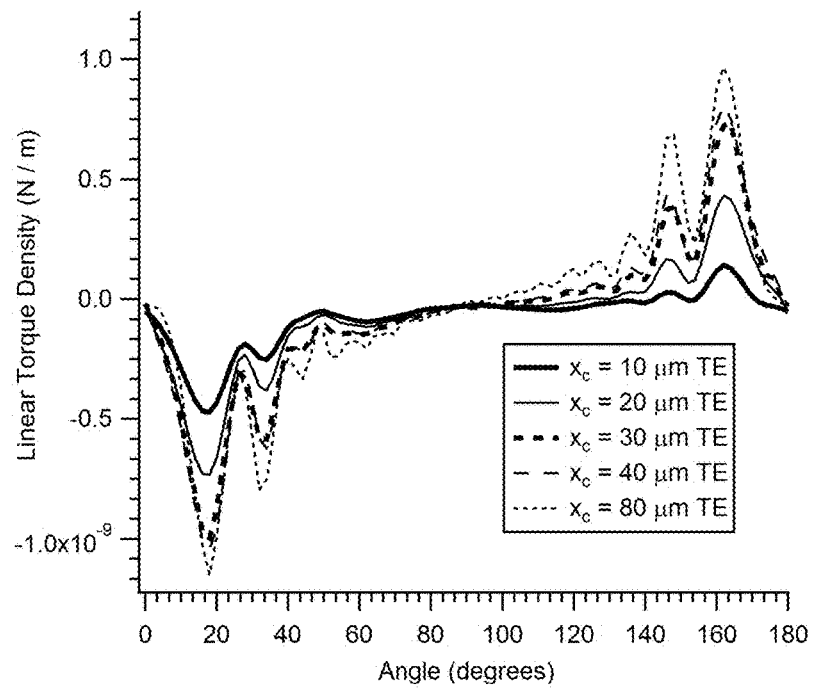
FIG. 8 shows torque on elliptical cylinder in water at a variety of distances from the terminus of a waveguide, referred to on the subsequent description of experimental work.
Figure 9:
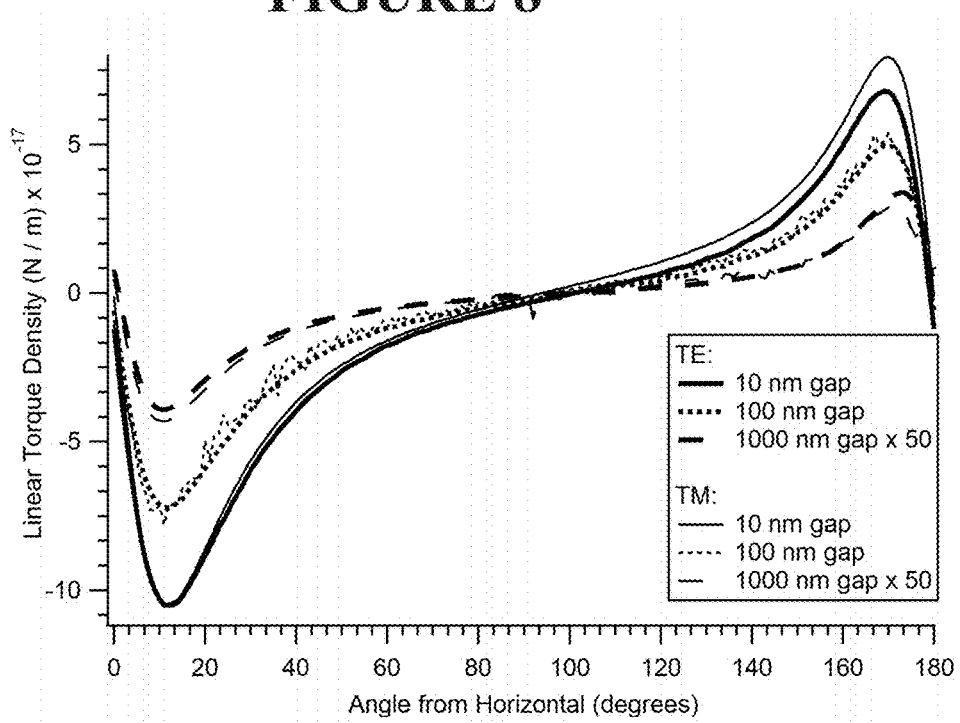
FIG. 9 shows torque on an elliptical cylinder in water above a waveguide at 3 separation distances, referred to on the subsequent description of experimental work.
Figure 10:
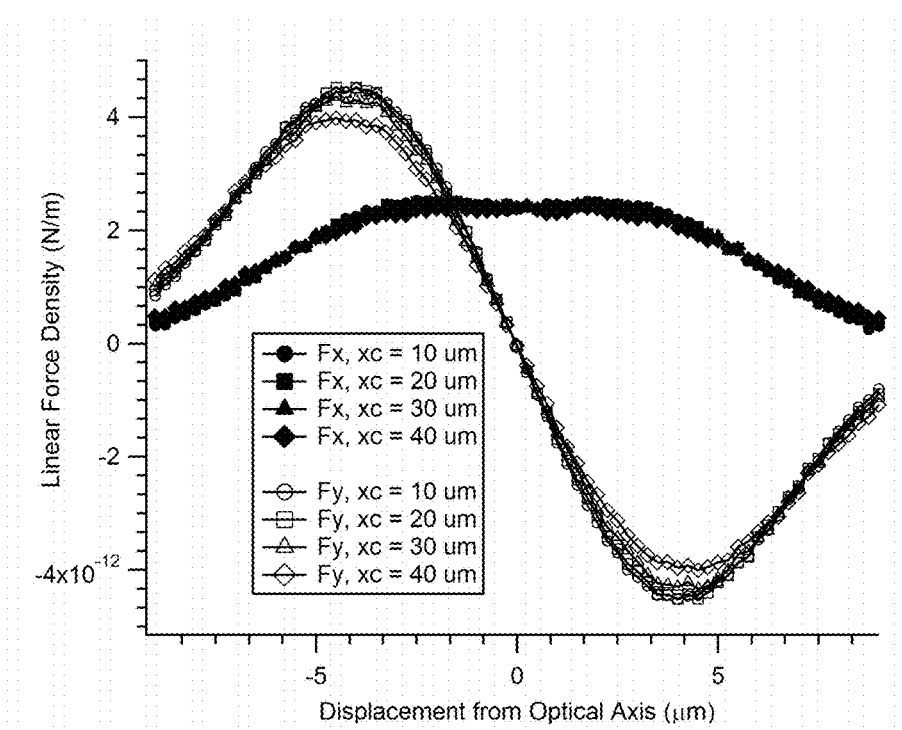
FIG. 10 shows Fx and Fy forces on an elliptical cylinder in water at the terminus of a waveguide in the vertical orientation for a variety of separation distances, referred to on the subsequent description of experimental work.
Figure 11:
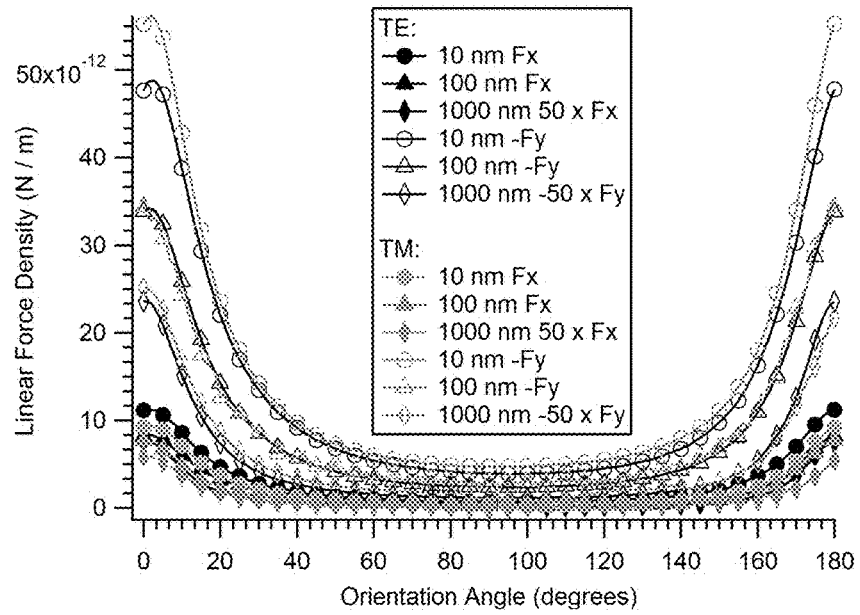
FIG. 11 shows Fx and Fy optical forces on an elliptical cylinder in water above a waveguide for a variety of separation distances, referred to on the subsequent description of experimental work.

Simulations were conducted using the finite element method (FEM) to approximate the action of optical forces on asymmetric particles. Specifically, the optical forces applied to elliptical particles situated near waveguides such as those described above were calculated. The orienting angular torques were calculated and the trapping/propulsive forces were also calculated. 2-dimensional (2D) approximations of elliptical particles (a cylinder) with a 10 μm:2 μm major:minor axis were placed at the terminus of the 2D approximation of a single mode optical optical fiber, a slab waveguide—FIG. 7a. The resulting torque applied to such an elliptical particle as a function of its orientation with respect to the waveguide optical axis is shown in FIG. 7b. The applied input power in the waveguide is 50 mW. Waveguide modes polarized parallel (TM) and perpendicular to (TE) the plane of simulation are shown. The same 2D particle approximation was placed above a 2D approximation of a ridge waveguide, as shown in FIG. 8, and the resulting torque as a function of orientation parallel to the waveguide optical axis is shown in FIG. 9. Both results show that the particle is oriented (has no applied torque) when its minor axis is parallel to the optical axis of the waveguides. That is, when it is in the vertical (angle=90°) orientation. Further the graphs show that the torque is restoring (in opposition to direction of motion) about that orientation angle. This is equilibrium orientation of the particle due to the applied optical forces. The resulting optical force applied to the above elliptical cylinder in water when at the terminus of a waveguide is shown in FIG. 10. The optical force applied to the same elliptical cylinder in water when above a waveguide is shown in FIG. 11. These optical forces are shown separated into direction parallel to (Fx) and perpendicular to (Fy) the waveguide optical axes for a variety of particle/waveguide separations for both TM and TE polarized waveguide modes. The particles are in the vertical/equilibrium orientation as described above.

Example 2

Figures 12A, 12B, 12C:
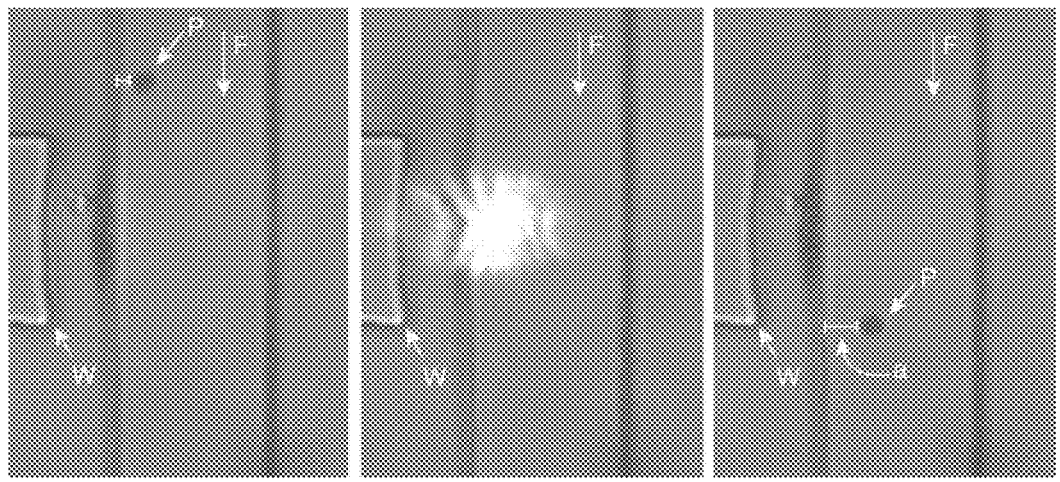
FIGS. 12*a-c* show symmetrical particle displacement by an optical field as the particle flows past the end of a wave-guide terminus in a microfluidic channel referred to on the subsequent description of experimental work, FIGS. 13*a* and *b* show an asymmetrical particle displacement by, and oriented by an optical field as the particle flows past the end of a wave-guide terminus in a microfluidic channel, referred to on the subsequent description of experimental work.

The images of FIGS. 12a-c which show symmetrical particle displacement by an optical field as a particle P moved past the end of a wave-guide terminus W in a 100 μm wide rectangular microfluidic channel flow F were collected with a 10× microscope objective imaged onto a CMOS digital camera sensor. The particle was a 10 μm diameter polystyrene spherical bead, and is shown flowing from top to bottom in FIG. 12. FIG. 12a shows the particle in the fluid flow before the waveguide. The particle interacted with the optical beam (250 mW of 532 nm coupled into a single mode fibre at >50% efficiency) diverging from the waveguide terminus. This interaction generated the strong scattering seen saturating the image of FIG. 12b. The optical force pushed the particle by displacement d as shown in FIG. 12c without stopping the flow of the particle along the microfluidic channel.

Example 3

Figures 13A, 13B:
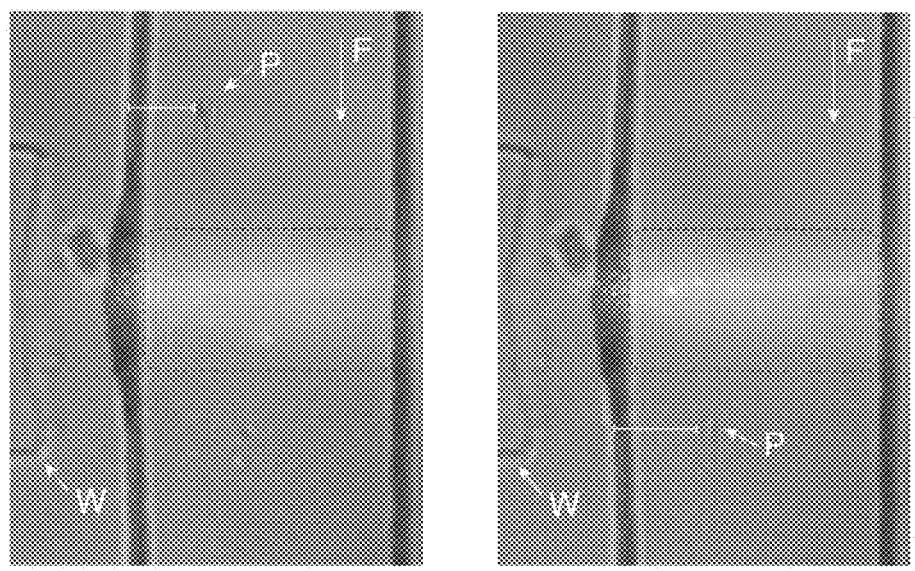

FIG. 13 illustrates the orienting effects of the optical field at the terminus of a waveguide W adjacent to the wall of a microfluidic channel. A particle P with an asymmetric shape specifically a bovine spermatozoa, was carried in a fluid flow from top to bottom in a fluid flow F in a microfluidic channel. The particle was inert and unable to move under its own propulsion. As shown in FIG. 13a the spermatozoa initially presented a dark scattering orientation to the imaging system. After passing through and interacting with the optical field at the terminus of the optical waveguide (outlined in FIG. 13) the spermatozoa continued to flow down the microfluidic channel with a new orientation and a displacement from its initial position. The particle was moved away from the channel wall after the interaction and rotated to a new orientation, but continued to flow down the channel. The new orientation of the spermatozoa presented a white head, indicating a rotation of 90 degrees about the long axis of the particle after interacting with the optical field.

Figure 14A:
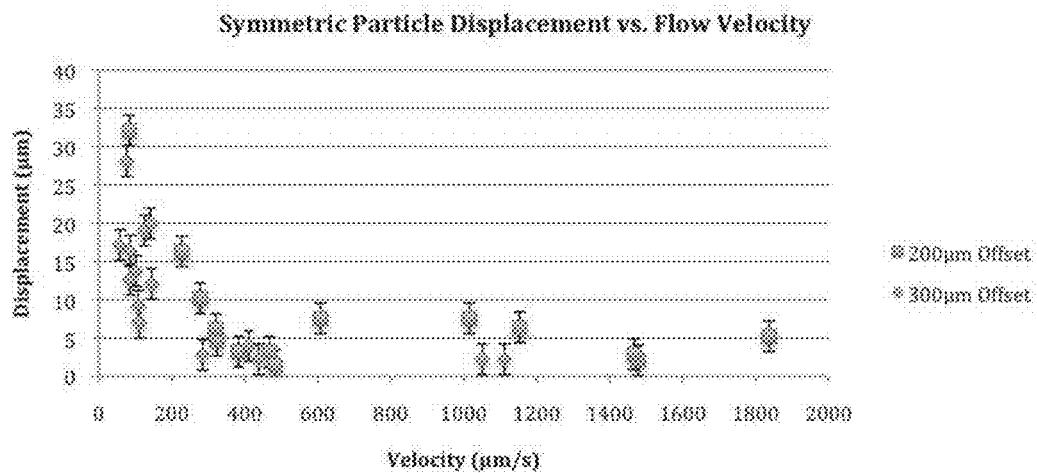
FIG. 14 shows the measured displacement efficiency as a function of particle flow speed for symmetric particles—FIG. 14*a*, and asymmetric particles—FIG. 14*b*.
Figure 14B:
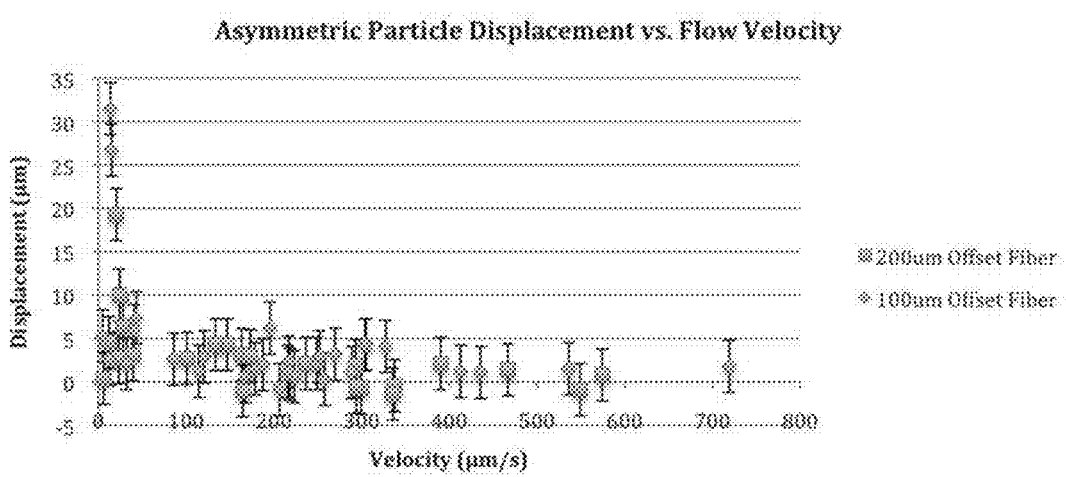

Multiple interaction events such as those observed in FIG. 12 and FIG. 13 were analysed frame-by-frame and the results presented in FIG. 14. Image processing was used to measure the particle position and orientation before and after interacting with the optical field. FIG. 14 shows the measured displacement efficiency as a function of particle flow speed for symmetric particles namely a 10 μm diameter polystyrene bead—FIG. 14a, and asymmetric particles namely non-motile bovine spermatozoa—FIG. 14b. For example these particles are flowing past the terminus of a single waveguide with less than 200 mW output power at a wavelength of 532 nm. Offset indicates distance from fibre termination to the edge of the microfluidic channel.

The invention claimed is:

1. A microfluidic system for sexing sperm comprising:
   at least one channel configured for flowing a fluid flow between at least one input source and at least two outputs;
   an orientation stage arranged downstream from the at least one input source, and comprising at least one optical waveguide configured to expose sperm contained in the flow to radiation pressure for causing at least a majority of the sperm to adopt a particular orientation in the flow;
   a detection stage arranged downstream from the orientation stage and comprising an optical detector configured to discriminate between X and Y sperm in the flow; and
   a switching stage comprising a plurality of optical waveguides arranged and configured to expose sperm in the flow to radiation pressure for causing a change in direction of movement of selected X or selected Y sperm in the flow so as to sort the selected X or selected Y sperm into one of the at least two outputs based on input from the detection stage.

2. The microfluidic system of claim 1, wherein the optical waveguides are connected to a laser or lasers.

3. The microfluidic system of claim 1, wherein the waveguides extend across the channel or abut the channel of the microfluidic system.

4. The microfluidic system of claim 1, further comprising a controller, wherein the controller is arranged to activate the radiation pressure from the optical waveguides.

5. The microfluidic system of claim 4, wherein the radiation pressure deflects sperm from a flow on one side, across a flow boundary or boundaries, and into a flow towards a selected output.

6. The microfluidic system of claim 1, wherein the optical detector is arranged to discriminate sperm by a fluorescence-based detection technique.

7. The microfluidic system of claim 1, further comprising a focusing stage, arranged before the orientation stage, in fluid communication with the at least one input source, the focusing stage comprising an apparatus configured to provide at least one of a hydrodynamic pressure force and a radiation pressure force, to focus the sperm to a particular location within the fluid.

8. The microfluidic system of claim 3, wherein the plurality of optical waveguides abut the channel from above, below or along the side walls of the channel.

9. The microfluidic system of claim 1, further comprising a cooling stage capable of cooling the fluid and the sperm within the fluid.

10. The microfluidic system of claim 1, wherein the at least one channel has a width of about 10 µm to about 500 µm.

11. The microfluidic system of claim 1, wherein the at least one channel has a depth of about 5 µm to about 500 µm.

12. A method of sexting sperm in a microfluidic system, comprising,
   forcing sperm to adopt a particular orientation in fluid flow within at least one channel of the microfluidic system by contacting the sperm with a radiation force produced by at least one optical waveguide;
   following orientation, discriminating between X and Y sperm in the fluid flow; and
   causing a change in the direction of movement of selected X or selected Y sperm in the fluid flow to sort the selected X or selected Y sperm into one of at least two output sources,
   wherein the change in direction is caused by contacting the selected X or selected Y sperm with a radiation force produced by a plurality of optical waveguides.

13. The microfluidic system of claim 1, wherein the plurality of optical waveguides for the switching stage are sequentially arranged.

* * * * *